United States Patent [19]

Jagdmann et al.

[11] Patent Number: 5,236,931
[45] Date of Patent: Aug. 17, 1993

[54] 2-SUBSTITUTED BENZAMIDE AND BENZOATE DERIVATIVES OF 3-AMINOQUINUCLIDINE AND 3-QUINUCLIDINOL

[75] Inventors: Gunnar E. Jagdmann, Apex, N.C.; Harry R. Munson, Jr., Leawood, Kans.

[73] Assignee: A. H. Robins Company, Incorporated, Richmond, Va.

[21] Appl. No.: 858,260

[22] Filed: Mar. 26, 1992

[51] Int. Cl.$^5$ .................. A61K 31/445; C07D 451/12
[52] U.S. Cl. .................. 514/305; 514/872; 546/133; 546/137
[58] Field of Search .............. 546/133, 137; 514/305, 514/872

[56] References Cited

U.S. PATENT DOCUMENTS

| | | | |
|---|---|---|---|
| 4,593,034 | 6/1986 | Munson | 514/305 |
| 4,657,911 | 4/1987 | Imbert | 514/272 |
| 4,803,199 | 2/1989 | Donatsch | 514/214 |
| 4,877,780 | 10/1989 | Vega-Noverola | 514/161 |

FOREIGN PATENT DOCUMENTS

| | | |
|---|---|---|
| 0200444 | 10/1985 | European Pat. Off. . |
| 0235878 | 10/1986 | European Pat. Off. . |
| 0214772 | 3/1987 | European Pat. Off. . |
| 0220011 | 4/1987 | European Pat. Off. . |
| 0306345 | 3/1989 | European Pat. Off. . |
| 2125398 | 3/1984 | United Kingdom . |
| 2152049 | 7/1985 | United Kingdom . |
| 2205095 | 5/1987 | United Kingdom . |

OTHER PUBLICATIONS

Mikhlina, Khim. Farmatsevt. Zh. No. 8, 20–24 (1973).
Costall et al., Pharmac. Ther. 47, 181–202 (1990).
Barnes et al., Nature 338, 762–3 (1989).
Pavia, "Cognition Enhancers," Ann. Repts. Med. Chem. 25, 21 (1989).

Primary Examiner—Marianne M. Cintins
Assistant Examiner—Catherine S. Kilby Scalzo
Attorney, Agent, or Firm—R. F. Boswell, Jr.

[57] ABSTRACT

This invention provides novel 3-quinuclidinyl benzamides and benzoates which have utility as therapeutical agents which exhibit anxiolytic, antipsychotic, cognition improvement, antiemetic and gastric prokinetic effects in warm blooded animals.

The compounds useful in the methods and composition of this invention are represented by the formula:

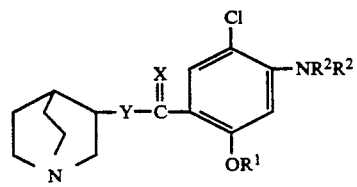

where X is oxygen or sulfur; Y is —NH or —O—; when Y is —O—, $R^1$ is

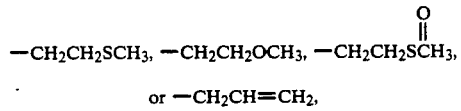

or —CH$_2$CH=CH$_2$, and when Y is —NH, $R^1$ is

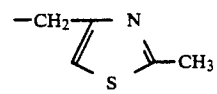

and $R^2$ is hydrogen, $C_1$–$C_4$ alkyl or $C_1$–$C_4$ alkenyl; the geometrical and optical isomers, or a pharmaceutically acceptable salt thereof.

18 Claims, No Drawings

2-SUBSTITUTED BENZAMIDE AND BENZOATE DERIVATIVES OF 3-AMINOQUINUCLIDINE AND 3-QUINUCLIDINOL

BACKGROUND OF THE INVENTION

Quinuclidine analogs of sulpiride were prepared and studied by Mikhlina, E. E. et al as reported in Khim-Farmatsevt, Zh. 10, No. 11, 56-60 (1976); C.A. 86: 155489r exemplified by the compound: 5-aminosulfonyl-N-(1-azabicyclo[2.2.2]oct-3-yl)-2-methoxybenzamide. The above named compound was reported in USSR Pat. No. SU414-261 to have neuroleptic activity.

Synthesis of 4-amino-N-(1-azabicyclo[2.2.2]oct-3-yl)-benzamide and N-(1-azabicyclo[2.2.2]oct-3-yl)benzamide were reported by Mikhlina, E. E. et al in Khim-Farmatsevt. Zh 7, 20-24 (1974); C.A. 79: 146358a and the latter in Khim. Geterosikl. Soedin., Akad. Nauk. Latv. SSR 243-9 (1966); C.A. 65: 2220b. The compounds were reported to exhibit hypotensive, narcotic and ganglionic stimulation and blocking activities, properties not seen in the compounds of the present invention.

Synthesis of 4-amino-N-(1-azabicyclo[2.2.2]oct-3-yl)-3-chloro-5-trifluoromethylbenzamide was reported in Ger. Offen. No. 2,548,968; C.A. 87: 68001c and equivalently related U.S. Pat. No. 4,093,734 from 4-amino-3-chloro-5-trifluoromethyl-benzoic acid chloride and 3-aminoquinuclidine. The compound is in a class among pyrrolidinyl and piperidinyl benzamides which are said to be useful as anxiolytics, anticonvulsives, antiemetics and antiulcerogenics.

G.B. 2,160,871A describes ether and thioether benzamide derivatives of dialkylaminoalkylamine or 1-alkyl-4-aminopiperidines that are useful in the treatment of emesis, and also the treatment of impaired gastric motility disorders. The patent compounds are analogs of metoclopramide and clebropride.

U.S. Pat. Nos. 4,593,034; 4,657,911; and 4,717,563 describe benzamide derivatives of 1-azabicyclo[2.2.2]octan-3-amine (3-aminoquinuclidine) and benzoate derivatives of 1-azabicyclo[2.2.2]octan-3-ol (3-quinuclidinol) which exhibit gastric prokinetic and antiemetic effects in warm blooded animals.

U.S. Pat. Nos. 4,722,834 and 4,820,715 describe 3-quinuclidinyl benzamides which are useful for the control of emesis caused by administration of anticancer drugs to warm blooded animals.

European Patent Applications 200-444; 235-878; 214-772; and 254-854; and British Patent Application 2152049 and 2125398 describe novel quinuclidine derivatives which exhibit serotonin antagonist activities, and are indicated for the treatment of pain and/or CNS disorders in warm blooded animals.

European Patent Application 306-345 describes 2-alkoxy-N-(1-azabicyclo[2.2.2]oct-3-yl)benzamides and thiobenzamides having antischizophrenic activity.

There is continuing interest in the development of quinuclidine derivatives which exhibit a novel combination of therapeutic properties for the treatment of disorders in warm blooded animals, with minimal neuropharmacological side effects.

Accordingly, it is an object of this invention to provide novel 3-quinuclidinyl benzamide and benzoate compounds with exhibit therapeutic properties for the treatment of warm blooded animals.

Accordingly, it is another object of this invention to provide pharmaceutical compositions containing a therapeutic dosage of a 2-substituted benzoic acid derivative of 3-aminoquinuclidine or 3-quinuclidinol which exhibit selective 5-HT(serotonin) antagonist effects in warm blooded animals.

It is another object of this invention to provide a method for the treatment of warm blooded animals for anxiety or pyschosis or other CNS disorders.

It is another object of this invention to provide a method for the treatment of warm blooded animals for the improvement of cognition function.

It is another object of this invention to provide a method for the treatment of warm blooded animals to alleviate migraine, cluster headache or trigeminal neuralgia symptoms.

It is a further object of this invention to provide a method for the treatment of emesis or impaired gastrointestinal motility in warm blooded animals.

Other objects and advantages of the present invention shall become apparent from the accompanying description and examples.

DESCRIPTION OF THE INVENTION

One or more objects of the present invention are accomplished by the provision of 3-quinuclidinyl benzamide and benzoate derivatives corresponding to the formula:

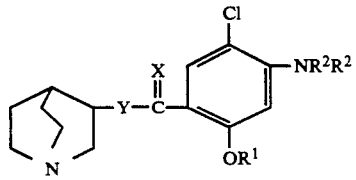

where X is oxygen or sulfur; Y is —NH or —O—; when Y is —O—, R is

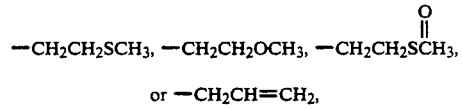

or —CH$_2$CH=CH$_2$, and when Y is —NH, R$^1$ is

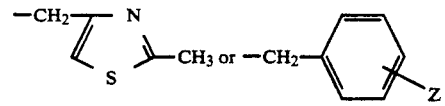

where Z is H, chlorine, bromine or iodine; and R$^2$ is hydrogen, C$_1$-C$_4$ alkyl or C$_1$-C$_4$ alkenyl; the geometrical and optical isomers, or a pharmaceutically acceptable salt thereof.

Illustrative of C$_1$-C$_4$ alkyl and C$_1$-C$_4$ alkenyl in the above formula are methyl, ethyl, propyl, isopropyl, butyl, isobutyl, 2-butyl, ethenyl, 2-propenyl, 2-butenyl, and the like. The term "pharmaceutically acceptable acid addition salts" as employed herein refers to the acid addition salts, hydrates, alcoholates and salts of the compounds represented by Formula I which are physiologically compatible in warm blooded animals. The acid addition salts are formed with inorganic and organic acids such as hydrochloric, sulfuric, phosphoric, fumaric, maleic, succinic, oxalic, citric, tartaric, cyclohexamic, and the like.

The invention compounds in the form of optical isomeric mixtures can be isolated as pure isomer fractions by conventional resolution procedures. Pure isomeric products also can be synthesized directly by employing appropriate chiral precursors.

The quinuclidine derivatives of the present invention can be effective in the treatment of disorders associated with an imbalance of 5-HT(serotonin), by inhibition or modulation of selective 5-HT activities, and thus can be useful in the treatment of migraine headaches, psychosis, and disorders of memory and learning.

In another embodiment this invention provides a method for the treatment of warm blooded animals for anxiety or psychosis symptoms which comprises internally administering to said animals a symptoms alleviating effective amount of a formulated quinuclidine derivative corresponding to Formula I as represented above.

In another embodiment this invention provides a method for the treatment of warm blooded animals for the improvement of cognition function which comprises internally administering to said animals a cognition function improving effective amount of a formulated quinuclidine derivative corresponding to Formula I as represented above.

In another embodiment this invention provides a method for the treatment of warm blooded animals for migraine, cluster headache or trigeminal neuralgia symptoms which comprises internally administering to said animals a symptoms alleviating effective amount of a formulated quinuclidine derivative corresponding to the Formula I as represented above.

In another embodiment this invention provides a method for the treatment of warm blooded animals for emesis caused by administration of anticancer drugs such as cisplatin during cancer treatment which comprises internally administering to said animals an emesis-inhibiting effective amount of a quinuclidine derivative corresponding to Formula I as represented above. An invention quinuclidine derivative also is applicable for the treatment of emesis caused by administration of non-platinum anticancer drugs such as mechlorethamine hydrochloride, doxrubicin, dactinomycin and dacarbazine.

In a further embodiment this invention provides a method for the treatment of warm blooded animals for impaired gastrointestinal motility which comprises internally administering to said animals a gastric motility-enhancing effective amount of a quinuclidine derivative corresponding to Formula I as represented above.

A present invention formulated composition of a Formula I compound is administered to warm blooded animals in a wide variety of conventional pharmaceutical dosage forms, preferably in combination with a non-toxic pharmaceutical carrier. The active agent is administered orally, subcutaneously, intravenously or intramuscularly or parenterally and, if necessary, in repeated doses until satisfactory response is obtained. The daily dosage is from about 0.001 to about 1000 mg of active medication, advantageously from about 0.01 mg to 50 mg.

Compositions for oral administration can be in the form of elixirs, capsules, tablets or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone.

For parenteral administration, the carrier or excipient can be comprised of a sterile parenterally acceptable liquid, e.g., water or arachis oil contained in ampoules.

The pharmaceutical compositions for use in alleviation of symptoms associated with anxiety, psychosis, cognitive function or migraine disorders will be formulated to contain from about 0.001 mg/kg to about 4.0 mg/kg body weight, preferably 1.0 mg/kg body weight or less of a compound of Formula I.

The pharmaceutical compositions for use in conjunction with administration of anticancer drugs in cancer treatment will be formulated to contain from about 0.1 mg/kg to about 50 mg/kg body weight, preferably 1.0 mg/kg body weight or less of a compound of Formula I.

In all of the above, it is only necessary that a suitable effective dosage is consistent with the dosage form employed. The exact individual dosages, as well as daily dosages, will be determined according to standard medical principles under the direction of a physician or veterinarian.

PREPARATION OF INVENTION COMPOUNDS

A quinuclidine derivative of the present invention can be prepared by reacting a substituted benzoyl intermediate with 3-aminoquinuclidine or 3-quinuclidinol, and can be converted into corresponding thiobenzamides.

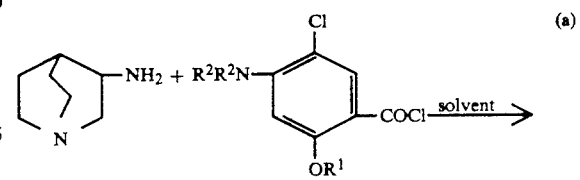

(a)

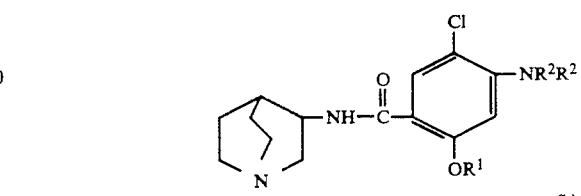

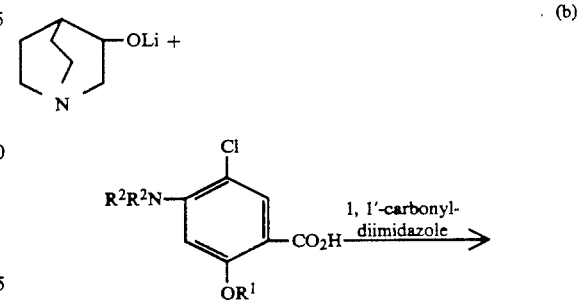

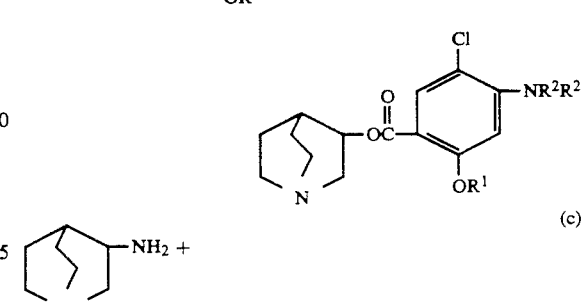

(b)

(c)

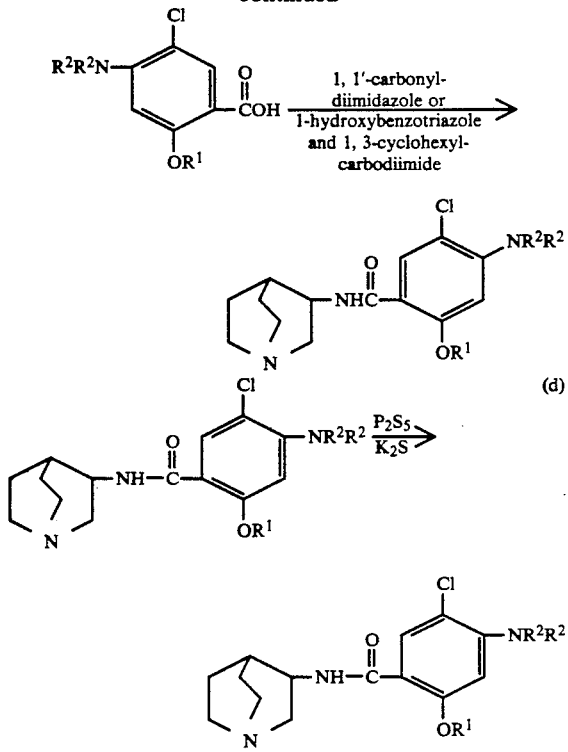

The following examples are further illustrative of the present invention. The components and specific ingredients are presented as being typical, and various modifications can be derived in view of the foregoing disclosure within the scope of the invention.

INTERMEDIATE 1

4-Amino-5-chloro-2-hydroxybenzoic acid, methyl ester

A. 4-Amino-5-chloro-2-hydroxybenzoic acid

A cooled (5° C.) suspension of 60% sodium hydride/oil dispersion (20 g, 0.5 mole) in anhydrous dimethylformamide (300 ml) under nitrogen was treated dropwise with ethyl mercaptan (18.7 g, 0.3 mole) while maintaining a temperature below 15° C., then stirred at room temperature for 15 minutes, cooled (5° C.), and treated in portions with 4-amino-5-chloro-2-methoxybenzoic acid (40.33 g, 0.2 mole). The mixture was heated to 105°±5° C. for 4 hours, cooled, and concentrated in vacuo to remove most of the dimethylformamide, then poured into water (500 ml). The aqueous solution was extracted with methylene chloride (2×150 ml), and ether (150 ml), acidified with concentrated HCl (55 ml), filtered, and the filter cake washed with water and dried in vacuo to provide 35.7 g of crude product. Crystallization of the product from tetrahydrofuran/hexane yielded 31.3 g (83%) of a white solid, mp 192° C.

B. 4-Amino-5-chloro-2-hydroxybenzoic acid, methyl ester

A solution of 4-amino-5-chloro-2-hydroxybenzoic acid (1.88 g, 10 mmoles) in absolute methanol (20 ml) was treated with 25% sodium methoxide/methanol (2.16 g, 10 mmoles), stirred for 30 minutes, and concentrated in vacuo. The solid residue was dissolved in anhydrous acetone (30 ml), treated with dimethyl sulfate (1.64 g, 13 mmoles), and refluxed for 2 hours. The resultant solution was diluted with water (100 ml), and the precipitate was filtered, washed with water, and dried in vacuo to yield 1.75 g (87%) of fine colorless needles. The product was recrystallized from ethyl acetate/hexane, mp 138°-139° C.

Anal. Calc. for $C_8H_8ClNO_3$: C, 47.66; H, 4.00; N, 6.95. Found: C, 47.60; H, 4.00; N, 6.93.

INTERMEDIATE 2

4-Amino-5-chloro-2-[2-(methylthio)ethoxy]benzoic acid

A cooled (5° C.) suspension of 60% sodium hydride oil dispersion (0.52 g, 13 mmole) in anhydrous dimethylformamide (15 ml) under nitrogen was treated in portions with 4-amino-5-chloro-2-hydroxybenzoic acid (0.94 g, 5 mmoles) stirred for 15 minutes at 25° C., treated with (2-chloroethyl)methyl sulfide (1.66 g, 15 mmoles), and heated to 100°±5° C. for 18 hours. The solution was cooled, concentrated in vacuo to remove most of the dimethylformamide and water (25 ml) was added. The aqueous solution was extracted with ether (2×25 ml), and the combined extracts were dried (MgSO4), concentrated in vacuo, taken up in 50% aqueous ethanol (50 ml), treated with potassium hydroxide (5.0 g), and refluxed for one hour. The mixture was concentrated to remove most of the ethanol, diluted with water to 75 ml total volume, extracted with ether (2×35 ml), and acidified to pH 3 with concentrated HCl. The resultant precipitate was filtered, washed with water, air dried, and recrystallized from ethyl acetate to yield 0.75 g (57%) of fine voluminous white needles, mp 137.5°-139.5° C.

Anal. Calc. for $C_{10}H_{12}ClNO_3S$: C, 45.89; H, 4.62; N, 5.35. Found: C, 45.96; H, 4.72; N, 5.32.

INTERMEDIATE 3

4-Amino-5-chloro-2-(2-methoxyethoxy)benzoic acid

A. 4-Amino-5-chloro-2-(2-methoxyethoxy)benzoic acid, methyl ester

A suspension of 60% sodium hydride/oil dispersion (1.0 g, 25 mmoles) in anhydrous dimethylformamide (40 ml) under nitrogen was treated with methyl 4-amino-5-chloro-2-hydroxybenzoate (4.03 g, 20 mmoles), stirred for 30 minutes, then treated with 2-bromoethyl methyl ether (3.48 g, 25 mmoles). The mixture was heated to 95°±5° C. for 1.5 hours, then cooled and added to water (250 ml). The aqueous suspension was filtered, and the solid was washed with water, air dried, and recrystallized from ether/hexane to yield 2.75 g (53%) of product, 121°-122.5° C.

B. 4-Amino-5-chloro-2-(2-methoxyethoxy)benzoic acid

A solution of 4-amino-5-chloro-2-(2-methoxyethoxy)-benzoic acid methyl ester (2.75 g, 10.6 mmoles) in 95% ethanol (20 ml) was treated with 50% sodium hydroxide (10 ml) and water (10 ml), and refluxed for one hour. The ethanol was removed in vacuo and replaced with water, and the aqueous solution was extracted with ether (20 ml) and adjusted to pH 4 with concentrated hydrochloric acid (16 ml). A resultant precipitate was filtered, washed with water, air dried, and recrystallized from ethyl acetate to yield 2.03 g (78%) of fine pale tan needles, mp 119°-120° C.

Anal. Calc. for $C_{10}H_{12}ClNO_4$: C, 48.89; H, 4.92; N, 5.70. Found: C, 48.87; H, 4.94; N, 5.68.

INTERMEDIATE 4

4-Amino-5-chloro-2-[(2-methylthiazol-4-yl)methoxy]-benzoic acid

A suspension of 60% sodium hydride/oil dispersion (0.5 g, 12.5 mmoles) in anhydrous dimethylformamide (20 ml) under nitrogen was treated with methyl 4-amino-5-chloro-2-hydroxybenzoate (2.02 g, 10 mmoles), stirred for 30 minutes, then treated with 4-chloromethyl-2-methylthiazole (1.85 g, 12.5 mmoles). The mixture was heated to 95°±5° C. for 1.5 hours, then cooled and added to water (150 ml). The aqueous mixture was extracted with ether (2×100 ml), and the combined ethereal solution was dried (MgSO$_4$), concentrated in vacuo, and taken up in 95% ethanol (20 ml). Water (10 ml) and 50% sodium hydroxide (10 ml) were added, and the mixture was refluxed for one hour, cooled in on ice, and concentrated in vacuo to remove most of the ethanol. Water was added to a total volume of 100 ml, and the aqueous solution was extracted with ether (2×50 ml), cooled in an ice bath, and adjusted to pH 4 with concentrated hydrochloric acid (16 ml). A resultant precipitate was filtered, washed with water, air dried, and recrystallized from 95% ethanol to yield 1.96 g (64%) of tan crystals, mp 188°–189° C.

Anal. Calc. for $C_{12}H_{11}ClN_2O_3S.\frac{1}{2}H_2O$: C, 46.83; H, 3.93; N, 9.10. Found: C, 46.92; H, 3.99; N, 3.99.

INTERMEDIATE 5

4-Amino-5-chloro-2-(phenylmethoxy)benzoic acid

A cooled (0°) suspension of 60% sodium hydride/oil dispersion (7.2 g, 180 mmol) in anhydrous N,N-dimethylformamide (200 mL) under nitrogen was treated in portions with 4-amino-5-chloro-2-hydroxybenzoic acid, methyl ester (30.24 g, 150 mmol) so as to keep the pot temperature below 20° C. After one hour at 40° C., the mixture was treated with benzyl bromide (30.8 g, 180 mmol) and heated to 100°±5° C. for one hour, then cooled to room temperature and added to water (600 mL). The aqueous solution was extracted with methylene chloride (3×250 mL), and the combined organic solution was dried (Na$_2$SO$_4$), concentrated in vacuo, and filtered through a short column of alumina (eluted with methylene chloride). The filtrate was concentrated in vacuo, taken up in a mixture of 50% sodium hydroxide (50 mL), water (50 mL), and ethanol (100 mL), and refluxed for one hour. Most of the ethanol was removed in vacuo and water (400 mL) was added to dissolve all solid. The aqueous solution was extracted with ether (100 mL), then with petroleum ethers (30° C.–60° C., 100 mL), cooled (0° C.), and acidified to pH 3 with concentrated hydrochloric acid (about 90 mL). The resultant precipitate was filtered and the solid was washed with water, air dried, and recrystallized (2 crops) from ethanol to afford 25.51 g (61%) of tan crystals; mp 182°–184° C.

Analysis Calc. for $C_{14}H_{12}ClNO_3$: C, 60.55; H, 4.36; N, 5.04. Found: C, 60.55; H, 4.31; N, 5.35.

INTERMEDIATE 6

4-Amino-5-chloro-2-[(3-chlorophenyl)methoxy]benzoic acid

A cooled (0° C.) suspension of 60% sodium hydride/oil dispersion (7.2 g, 180 mmol) in anhydrous N,N-dimethylformamide (200 mL) under nitrogen was treated in portions with 4-amino-5-chloro-2-hydroxybenzoic acid, methyl ester (30.24 g, 150 mmol) so as to keep the pot temperature below 20° C. After one hour at 40° C., the mixture was treated with 3-chlorobenzyl bromide (37.0 g, 180 mmol) and heated to 100°±5° C. for one hour, then cooled to room temperature and added to water (600 mL). A solid precipitate soon formed, which was collected, washed with water, partially air dried, and dissolved in methylene chloride. The solution was filtered through alumina (eluted with methylene chloride) and the filtrate was concentrated in vacuo. The residue was taken up in a mixture of 50% sodium hydroxide (50 mL), water (50 mL), and ethanol (100 mL), and refluxed for one hour. Most of the ethanol was removed in vacuo and water (400 mL) was added to dissolve all solid. The aqueous solution was extracted with ether (100 mL), then with petroleum ethers (30°–60° C., 100 mL), cooled (0° C.), and acidified to pH 3 with concentrated hydrochloric acid (about 90 mL). The resultant precipitate was collected and the solid was washed with water, dried, and recrystallized (2 crops) from ethanol to afford 28.36 g (61%) of pale tan solid; mp 182.5°–184.0° C.

Analysis Calc. for $C_{14}H_{11}Cl_2NO_3$: C, 53.87; H, 3.55; N, 4.49. Found: C, 53.84; H, 3.48; N, 4.47.

INTERMEDIATE 7

4-Amino-5-chloro-2-[(3-iodophenyl)methoxy]benzoic acid

A cooled (0° C.) suspension of 60% sodium hydride/oil dispersion (1.32 g, 33 mmol) in anhydrous N,N-dimethylformamide (45 mL) under nitrogen was carefully treated in portions with 4-amino-5-chloro-2-hydroxybenzoic acid, methyl ester (6.05 g, 30 mmol), maintained at 40°–45° C. for 1 hour, then treated with 3-iodobenzyl bromide (10.7 g, 36 mmol) and heated to 100°±5° C. for 1 hour. The solution was cooled and added to ice water (250 mL), and after a few minutes, a precipitate formed which was collected. The solid was washed with water, air dried, and taken up methylene chloride and filtered through alumina (eluted with 5% methanol/methylene chloride). The filtrate was concentrated in vacuo and the residue was triturated from petroleum ethers (30° C.–60° C.). The solid was taken up in 50% aqueous methanol (200 mL), treated with 50% sodium hydroxide (22 g), refluxed for 3 hours, and concentrated in vacuo to remove most of the methanol. The resultant suspension was cooled on an ice bath, treated with concentrated hydrochloric acid to pH 3 (about 30 mL), then filtered. The solid was washed with water, air dried overnight, and triturated from acetonitrile to afford 8.10 g (67%) of pale orange solid; mp 172°–173° C. (EtOH/MeOH).

Analysis Calc. for $C_{14}H_{11}ClINO_3$: C, 41.66; H, 2.75; N, 3.47. Found: C, 41.67; H, 2.71; N, 3.46.

EXAMPLE I

4-Amino-N-(1-azabicyclo[2,2,2]oct-3-yl)-5-chloro-2-[(2-methylthiazol-4-yl)methoxy]benzamide A suspension of 4-amino-5-chloro-2-[(2-methylthiazol-4-yl)methoxy]benzoic acid (1.54 g, 5 mmoles) in anhydrous tetrahydrofuran (5 ml) was treated with 1,1'-carbonyldiimidazole (0.89 g, 5.5 mmoles), stirred at room temperature for 90 minutes, then added to a cooled (0° C.) solution of 3-aminoquinuclidine (from 6 mmoles of dihydrochloride salt and 12 mmoles of 25% sodium methoxide/methanol) in anhydrous tetrahydrofuran (5 ml) under nitrogen. After 3 hours at room temperature and one hour at 60° C., the solution was concentrated in vacuo and partitioned between methylene chloride (50 ml) and 1.5N sodium hydroxide (20 ml). The organic layer was washed with 1.5N sodium hydroxide (20 ml), saturated sodium bicarbonate (20 ml), and brine (20 ml), dried ($Na_2SO_4$), and concentrated in vacuo. Filtration through alumina (eluted with 10% methanol/methylene chloride) provided 1.35 g (66%) of a colorless foam.

Fumaric Acid Salt

A solution of the above prepared compound (1.3 g, 3.19 mmoles) in absolute ethanol (15 ml) was treated with furmaric acid (0.75 g, 6.4 mmoles). After formation of a precipitate, ether (15 ml) was added. The solid was filtered and recrystallized from absolute ethanol to yield 1.1 g (66%) of a pale tan solid, mp 189°–190° C.

Anal. Calc. for $C_{19}H_{23}ClN_4O_2S.C_4H_4O_4$: C, 52.82; H, 5.20; N, 10.72. Found: C, 52.70; H, 5.45; N, 10.38.

(R)-(+)-4-Amino-N-(1-azabicyclo[2,2,2]oct-3-yl)-5-chloro-2-[(2-methyl-4-thiazolyl)methoxy]benzamide A suspension of anhydrous 4-amino-5-chloro-2-[(2-methyl-4-thiazolyl)methoxy]benzamide (2.69 g, 9.0 mmol) in anhydrous tetrahydrofuran (10 mL) under nitrogen was treated with 1,1'-carbonyldiimidazole (CDI, 1.70 g, 10.5 mmol) and, after the solution had cleared and a precipitate began to form, anhydrous dimethylformamide (3 mL) was added. The mixture was stirred for one hour and degassed under a stream of nitrogen over 15 minutes. Meanwhile, a solution of (R)-3-aminoquinuclidine dihydrochloride (2.39 g, 12 mmol) in methanol (50 mL) was treated with 25% sodium methoxide/methanol (5.2 g, 24 mmol), stirred for 20 minutes at 45° C., filtered, and concentrated in vacuo and taken up in tetrahydrofuran (50 mL). The solution was filtered, concentrated exhaustively in vacuo, dissolved in anhydrous tetrahydrofuran (10 mL), and added to the CDI-adduct prepared above (suspension soon cleared after addition). After 18 hours at room temperature and two hours at 50° C., the mixture was partitioned between saturated aqueous sodium carbonate (50 mL) and toluene (75 mL) containing some 2-propanol. The organic layer was separated and the aqueous solution was extracted with toluene (2×50 mL) containing some 2-propanol. The combined organic solution was dried ($Na_2SO_4$), concentrated in vacuo, and the viscous residue was washed with water, then dried by azeotropic removal of water with toluene. The residue was filtered through alumina (eluted with 4:1 tetrahydrofuran/methanol), and the filtrate was concentrated in vacuo and crystallized from ethyl acetate/hexane to afford 2.51 g (69%) of colorless crystals; mp 182°–183° C.; $[\alpha]_D^{22}$ +23.21° (C=1, methanol).

Anal. Calc. for $C_{19}H_{23}ClN_4O_2S$: C, 56.08; H, 5.70; N, 13.77. Found: C, 55.98; H, 5.77; N, 13.52.

S-(−)-4-Amino-N-(1-azabicyclo[2,2,2]oct-3-yl)-5-chloro-2-[(2-methyl-4-thiazolyl)methoxy]benzamide Following the procedure in the preceding paragraph, the S-(−) isomer is prepared from (S)-3-aminoquinuclidine in 83% yield; mp 182°–183° C.; $[\alpha]_D^{22}$ −23.01° (C=1, methanol).

Anal. Calc. for $C_{19}H_{23}ClN_4O_2S$: C, 56.08; H, 5.70; N, 13.77. Found: C, 56.00; H, 5.75; N, 13.66.

EXAMPLE II

4-Amino-5-chloro-2-[2-(methylthio)ethoxy]benzoic acid, ester with 1-azabicyclo[2.2.2]octan-3-ol A cooled (0° C.) solution of 3-quinuclidinol (1.72 g, 13.5 mmoles) in anhydrous tetrahydrofuran (15 ml) under nitrogen was treated with 2.50N n-butyllithium/hexane (13.0 mmoles), stirred for 30 minutes at room temperature, concentrated in vacuo, and dissolved in anhydrous tetrahydrofuran (10 ml) under nitrogen. A separate solution of 4-amino-5-chloro-2-[2-(methylthio)ethoxy]benzoic acid (3.14 g, 12 mmoles) in anhydrous tetrahydrofuran (15 ml) was treated with 1,1'-carbonyldiimidazole (2.01 g, 12.4 mmoles), stirred for one hour at room temperature, degassed with a stream of nitrogen, then added to the salt suspension prepared above. After 18 hours at 25° C. and one hour at 55° C., the mixture was concentrated in vacuo and partitioned between methylene chloride (100 ml) containing 2-propanol and 1.0N sodium carbonate (50 ml). The organic layer was separated and the aqueous solution was extracted with methylene chloride (2×50 ml). The combined organic solution was dried ($Na_2SO_4$), concentrated in vacuo, and filtered through alumina (eluted with 5% methanol/methylene chloride). The filtrate was concentrated in vacuo to provide 2.68 g (60%) of a colorless foam.

Fumarate Salt

A solution of the above prepared compound (1.66 g, 4.5 mmoles) in methanol (10 ml) was treated with a solution of fumaric acid (0.93 g, 8 mmoles) in methanol (20 ml), and the mixture was stirred for 5 minutes, filtered, and diluted with ether (50 ml). A crystalline solid formed, and the crystals were collected and dried to yield 1.8 g (83%) of a pale yellow solid, mp 119°–121° C.

Anal. Calc. for $C_{17}H_{23}ClN_2O_3S.C_4H_4O_4$: C, 51.80; H, 5.59; N, 5.75. Found: C, 51.70; H, 5.66; N, 5.67.

EXAMPLE III

4-Amino-5-chloro-2-(2-methoxyethoxy)benzoic acid, ester with 1-azabicyclo[2,2,2]octan-3-ol A cooled (0° C.) solution of 3-quinuclidinol (2.93 g, 23 mmoles) in anhydrous tetrahydrofuran (25 ml) under nitrogen was treated with 2.50N n-butyllithium/hexane (22 mmoles), stirred for 30 minutes at room temperature, concentrated in vacuo, and taken up in anhydrous tetrahydrofuran (20 ml) under nitrogen. A separate solution of 4-amino-5-chloro-2-(2-methoxyethoxy)benzoic acid (4.92 g, 20 mmoles) in anhydrous tetrahydrofuran (30 ml) was treated with 1,1'-carbonyldiimidazole (3.41 g, 21 mmoles), stirred for 30 minutes at 25° C., degassed with a stream of nitrogen, then added to the salt suspension prepared above. After 18 hours at room temperature, the mixture was concentrated in vacuo and partitioned between methylene chloride (150 ml) containing 2-propanol and 1.0N sodium carbonate (75 ml). The organic layer was separated and the aqueous solution was extracted with methylene chloride (50 ml). The combined organic solution was dried ($Na_2SO_4$), concentrated in vacuo, and filtered through alumina (eluted with 2% methanol/tetrahydrofuran). The filtrate was concentrated in vacuo and triturated from cold ether to provide 5.31 g (75%) of a colorless solid, mp 150°–153° C.

Fumarate Salt

A solution of the above prepared compound (3.55 g, 10 mmoles) in methanol (12 ml) was treated with fumaric acid (1.75 g, 15 mmoles) in methanol (20 ml), and the resultant solution was diluted to 100 ml total volume with ether. The resultant suspension was cooled, and the solid was collected and recrystallized from 2-propanol to yield 3.85 g (82%) of a voluminous white solid, mp 176°–177° C.

Anal. Calc. for $C_{17}H_{23}ClN_2O_4 \cdot C_4H_4O_4$: C, 53.56; H, 5.78; N, 5.95. Found: C, 53.50; H, 5.90; N, 5.84.

EXAMPLE IV

5-Chloro-4-(2-propenylamino)-2-(2-propenyloxy)benzoic acid, ester with 1-azabicyclo[2.2.2]octan-3-ol A. 5-Chloro-4-(2-propenylamino)-2-(2-propenyloxy)benzoic acid A suspension of 60% sodium hydride/oil (9.0 g, 225 mmoles) in anhydrous dimethylformamide (150 ml) under nitrogen was slowly treated with 4-amino-5-chloro-2-hydroxybenzoic acid (14.1 g, 75 mmoles) while maintaining a temperature below about 35° C., then stirred at room temperature for one hour. The mixture was treated with allyl bromide (36.3 g, 300 mmoles), then heated to 60° C. for 18 hours, cooled, and added to ice water (500 ml). The aqueous suspension was extracted with ether (3×200 ml), and the combined organic solution was concentrated in vacuo, dissolved in water (80 ml) and ethanol (20 ml), treated with potassium hydroxide (10.0 g, 178 mmoles), and refluxed for one hour. The ethanol was removed in vacuo and the aqueous solution was extracted with ether (2×50 ml), cooled (0° C.), and made acidic with concentrated HCl (about 18 ml). The aqueous solution was extracted with methylene chloride (2×150 ml), and the combined organic solution was dried (Na₂SO₄), concentrated in vacuo, and recrystallized from ethyl acetate/hexane to yield 10.21 g (51%) of a pale brown solid, mp 83.5°–86.0° C.

B. 5-Chloro-4-(2-propenylamino)-2-(2-propenyloxy)benzoic acid, ester with 1-azabicyclo[2.2.2]octan-3-ol A cooled (0° C.) solution of 3-quinuclidinol (3.44 g, 27 mmoles) in anhydrous tetrahydrofuran (25 ml) under nitrogen was treated with 2.5N n-butyllithium/hexane (26 mmoles), stirred for 30 minutes at room temperature, concentrated in vacuo, and taken up in anhydrous tetrahydrofuran (20 ml) under nitrogen. A separate solution of the above prepared compound (5.62 g, 21 mmoles) in anhydrous tetrahydrofuran (30 ml) was treated with 1,1'-carbonyldiimidazole (4.05 g, 25 mmoles), stirred for 30 minutes at 25° C., degassed with a stream of nitrogen, then added to the salt suspension prepared above. After 81 hours at room temperature, the mixture was concentrated in vacuo and partitioned between methylene chloride (150 ml) containing 2-propanol and 1.0N sodium carbonate (75 ml). The organic layer was separated and the aqueous solution was extracted with methylene chloride (50 ml). The combined organic solution was dried (Na₂SO₄), concentrated in vacuo, and filtered through alumina (eluted with 2% methanol/tetrahydrofuran). The filtrate was concentrated in vacuo and triturated from cold ether/petroleum ether (30°–60° C.) to yield 4.21 g (53%) of a colorless solid, mp 101.5°–103.5° C.

Fumarate Salt

A solution of the above prepared compound (3.02 g, 8 mmoles) in methanol (15 ml) was treated with fumaric acid (1.74 g, 15 mmoles) in methanol (25 ml). After 15 minutes at room temperature, the mixture was diluted with ether (160 ml), cooled, and filtered. The solid was recrystallized from 2-propanol, then from ethanol to yield 3.47 g (88%) of a colorless solid, mp 158°–159° C. Anal. Calc. for $C_{20}H_{25}ClN_2O_3$: C, 58.48; H, 5.93; N, 5.68. Found: C, 58.39; H, 5.90; N, 5.69.

EXAMPLE V

4-Amino-N-(1-azabicyclo[2.2.2]oct-3-yl)-5-chloro-2-(phenylmethoxy)benzamide

A solution of 4-amino-5-chloro-2-(phenylmethoxy)benzoic acid (2.78 g, 10 mmol) in anhydrous tetrahydrofuran (10 mL) under nitrogen was treated with 1,1'-carbonyldiimidazole (1.87 g, 11.5 mmol), stirred for 45 minutes, and degassed over 15 minutes under a stream of nitrogen. A solution of 3-aminoquinuclidine (1.84 g, 14.6 mmol) in anhydrous tetrahydrofuran (5 mL) was added, and the mixture was stirred at room temperature for 18 hours, then concentrated in vacuo and partitioned between 3N sodium hydroxide (50 mL) and toluene (100 mL) containing some 2-propanol. The organic layer was separated and the aqueous solution was extracted with toluene (50 mL) containing some 2-propanol. The combined organic solution was dried (Na₂SO₄), concentrated in vacuo and rinsed with water in order to remove the remainins imidazole by-product. The residue was dried azeotropically with toluene, then taken up in tetrahydrofuran and filtered through a short column of alumina (eluted with 10% methanol/tetrahydrofuran). The filtrate was concentrated in vacuo, triturated from cold ether/petroleum ethers (30°–60° C.), and recrystallized from ethyl acetate/hexane to afford 3.18 g (82%) of colorless solid; mp 170°–171° C.

Anal. Calc. for $C_{21}H_{24}ClN_3O_2$: C, 65.36; H, 6.27; N, 10.89. Found: C, 65.16; H, 6.30; N, 10.81.

EXAMPLE VI

4-Amino-N-(1-azabicyclo[2.2.2]oct-3-yl)-5-chloro-2-[(3-chlorophenyl)methoxy]benzamide A solution of 4-amino-5-chloro-2-[(3-chlorophenyl)methoxy]benzoic acid (3.13 g, 10 mmol) in anhydrous tetrahydrofuran (10 mL) under nitrogen was treated with 1,1'-carbonyldiimidazole (1.87 g, 11.5 mmol), stirred for 45 minutes, and degassed over 15 minutes under a stream of nitrogen. A solution of 3-aminoquinuclidine (1.85 g, 14.7 mmol) in anhydrous tetrahydrofuran (5 mL) was added, and the mixture was stirred at room temperature for 18 hours, then concentrated in vacuo and partitioned between 3N sodium hydroxide (50 mL) and toluene (100 mL) containing some 2-propanol. The organic layer was separated and the aqueous solution was extracted with toluene (50 mL) containing some 2-propanol. The combined organic solution was dried (Na₂SO₄), concentrated in vacuo, and rinsed with water in order to remove the remaining imidazole by-product. The residue was dried azeotropically with toluene, then taken up in tetrahydrofuran and filtered through a short column of alumina (eluted with 10% methanol/tetrahydrofuran). The filtrate was concentrated in vacuo, triturated from cold ether/petroleum ethers (30°–60° C.), and recrystallized from acetonitrile (2 crops) to afford 3.08 g (73%) of pale yellow solid; mp 168°–169° C.

Anal. Calc. for $C_{21}H_{23}Cl_2N_3O_2$: C, 60.01; H, 5.52; N, 10.00. Found: C, 59.97; H, 5.54; N, 10.12.

Example VII

4-Amino-N-(1-azabicyclo[2.2.2]oct-3-yl)-5-chloro-2-[(3-iodophenyl)methoxy]benzamide A mixture of 4-amino-5-chloro-2-[(3-iodophenyl)methoxy]benzoic acid (3.23 g, 8 mmol) and 1-hydroxybenzotriazole hydrate (1.23 g, 8 mmol) in anhydrous N,N-dimethylformamide (6 mL) under nitrogen was stirred for 30 minutes, treated with 1,3-dicyclohexylcarbodiimide (1.71 g, 8.3 mmol) in anhydrous N,N-dimethylformamide (2 mL), and stirred for 2 hours. A solution of 3-aminoquinuclidine (1.52 g, 12 mmol) in anhydrous N,N-dimethylformamide (4 mL) was added, and the mixture was stirred for 18 hours, filtered, and the filtrate concentrated in vacuo. The residue was dissolved in 20% methanol/tetrahydrofuran and filtered through a short column of alumina (eluted with 20% methanol/tetrahydrofuran). The filtrate was concentrated in vacuo and the residue was triturated from acetonitrile and recrystallized (2 crops) from 95% ethanol to afford 1.25 g (31%) of colorless solid; mp 196°–197° C.

Anal. Calc. for $C_{21}H_{23}ClIN_3O_2$: C, 49.28; H, 4.53; N, 8.21. Found: C, 49.35; H, 4.64; N, 8.08.

EXAMPLE VIII

(R)-(+)-4-Amino-N-(1-azabicyclo[2.2.2]oct-3-yl)-5-chloro-2-[(3-iodophenyl)methoxy]benzamide.

A solution of 4-amino-5-chloro-2-[(3-iodophenyl)methoxy]benzoic acid (3.23 g, 8.0 mmol) in anhydrous tetrahydrofuran (4 mL) and anhydrous N,N-dimethylformamide (4 mL) under nitrogen was treated with 1,1'-carbonyldiimidazole (1.46 g, 9.9 mmol), stirred for 45 minutes, and degassed over 15 minutes under a stream of nitrogen. A solution of (R)-3-aminoquinuclidine (1.54 g, 12.2 mmol) in anhydrous tetrahydrofuran (4 mL) was added, and the mixture was stirred at room temperature for 18 hours, warmed to 55°±5° C. for three hours, and concentrated in vacuo. The residue was partitioned between 3.0N sodium hydroxide (50 mL) and toluene (100 mL) containing some 2-propanol, and the organic layer was separated. The aqueous solution was extracted with toluene (50 mL) containing some 2-propanol, and the combined organic solution was concentrated in vacuo. The residue was washed with water to remove most of the imidazole, then dried azeotropically with toluene, taken up in tetrahydrofuran, and filtered through a short column of alumina (eluted with 10% methanol/tetrahydrofuran). The filtrate was concentrated in vacuo, taken up in warm acetone, and filtered. After a few hours, a solid had crystallized, and this was collected and dried in vacuo to afford (following second crop) 1.05 g (26%) of colorless solid; mp 101.5°–104° C., $[\alpha]_D^{22}$ +6.50° (C=1 in methanol).

Anal. Calc. for $C_{21}H_{23}ClIN_3O_2$: C, 49.28; H, 4.53; H, 8.21. Found: C, 48.87; H, 4.51; N, 8.08.

EXAMPLE IX

(S)-(−)-Amino-N-(1-azabicyclo[2,2,2]oct-3-yl)-5-chloro-2-[(3-iodophenyl)methoxy]benzamide A solution of 4-amino-5-chloro-2-[(3-iodophenyl)methoxy]benzoic acid (3.23 g, 8.0 mmol) in anhydrous tetrahydrofuran (4 mL) and anhydrous N,N-dimethylformamide (4 mL) under nitrogen was treated with 1,1'-carbonyldiimidazole (1.46 g, 9.9 mmol), stirred for 45 minutes, and degased over 15 minutes under a stream of nitrogen. A solution of (S)-3-aminoquinuclidine (1.54 g, 12.2 mmol) in anhydrous tetrahydrofuran (4 mL) was added, and the mixture was stirred at room temperature for 18 hours, warmed to 55°±5° C. for three hours, and concentrated in vacuo. The residue was partitioned between 3.0N sodium hydroxide (50 mL) and toluene (100 mL) containing some 2-propanol, and the organic layer was separated. The aqueous solution was extracted with toluene (50 mL) containing some 2-propanol, and the combined organic solution was concentrated in vacuo. The residue was washed with water to remove most of the imidazole, then dried azeotropically with toluene, taken up in tetrahydrofuran, and filtered through a short column of alumina (eluted with 10% methanol/tetrahydrofuran). The filtrate was concentrated in vacuo, taken up in warm acetone, and filtered. After a few hours, a solid had crystallized, and this was collected and dried in vacuo to afford (following second crop) 1.10 g (27%) of colorless solid; mp 101.5°–104° C., $[\alpha]_D^{22}$ −6.35° (C=1 in methanol).

Anal. Calc. for $C_{21}H_{23}ClIN_3O_2$: C, 49.28; H, 4.53; N, 8.21. Found: C, 48.97; H, 4.54; N, 8.10.

EXAMPLE X

4-Amino-5-chloro-2-(2-propenyloxy)benzoic acid ester with 1-azabicyclo-[2,2,2]octan-3-ol A cooled (0° C.) solution of quinuclidin-3-ol (1.91 g, 15 mmol) in anhydrous tetrahydrofuran (20 mL) under nitrogen was treated (via syringe) with 2.50N n-butyllithium/hexane (15 mmol), stirred for thirty minutes at room temperature, and concentrated in vacuo. Meanwhile, a suspension of 4-amino-5-chloro-2-(2-propenyloxy)benzoic acid (2.73 g, 12 mmol) in anhydrous tetrahydrofuran (10 mL) under nitrogen was treated with 1,1'-carbonyldiimidazole (2.11 g, 13 mmol), stirred for one hour, and transferred to the flask containing deprotonated quinuclidin-3-ol. The mixture was stirred for 18 hours at room temperature and for 90 minutes at 60° C., then concentrated in vacuo. The residue was partitioned between 1.0N sodium carbonate (100 mL) and toluene (150 mL) containing some 2-propanol, and the organic layer was separated. The aqueous solution was extracted with toluene (75 mL) containing some 2-propanol, and the combined organic solution was concentrated in vacuo. The residual oil was rinsed with water to remove the imidazole by-product, dried azeotropically with toluene, and taken up in anhydrous ether. The ethereal solution was filtered, and the filtrate concentrated in vacuo and passed through a short column of alumina (eluted with 5% methanol/tetrahydrofuran). The filtrate was concentrated in vacuo to afford 2.86 g (71%) of the product as a pale yellow viscous oil.

Hydrochloride Salt

A solution of 4-amino-5-chloro-2-(2-propenyloxy)-benzoic acid, ester with 1-azabicyclo[2.2.2]octan-3-ol (2.80 g, 8.3 mmol) in anhydrous ether (50 mL) was treated with excess ethereal HCl, then diluted with ethyl acetate (50 mL). After a few minutes, the suspension was filtered under nitrogen (hygroscopic), and the solid was washed with ethyl acetate, collected, and dried over 18 hours at 1 mm pressure and 80° C. in the presence of potassium hydroxide and phosphorus pentoxide. This afforded 2.76 g (87%) of the hydrochloride salt as the hemihydrate pale (yellow solid); mp 103°–105° C.

Anal. Calc. for $C_{17}H_{21}ClN_2O_3 \cdot HCl \cdot \frac{1}{2}H_2O$: C, 53.41; H, 6.06; N, 7.33. Found: C, 53.28; H, 6.02; N, 8.52.

BIOLOGICAL ACTIVITY

A. Anxiolytic Test Exploratory Light/Dark (mice)

The method has been described by Young and Johnson (1988) and is a modification of the procedure described by Costall and Naylor (1988). A two-compartment light-dark activity monitoring device (Digiscan Model RXYZCM16, Omnitech Electronics Inc., Columbus, Ohio) is used. A 90 W light source located 30 cm above the box provides light to the lit portion of the apparatus. Behavioral testing is conducted in a sound-attenuated, darkened room illuminated with red light (25 W red bulb) only.

Each animal (mouse) receives a dose or doses of either the test, reference, or control article. The animal is placed at the center of the illuminated area and the behavioral activity tallied over a 5 minute period by use of the Digiscan analyzer. Behavioral variables recorded included: the time spent in the lit and dark areas, the number of rearings in the lit and dark areas, the number of locomotor activity counts in the lit and dark areas, the number of transitions between the lit and dark or dark and lit areas, the latency to make the first transition from the lit area to the dark area, rearing time in the lit and dark areas, locomotor time in the lit and dark areas, and resting time in the lit and dark areas. Appropriate statistical analyses for each measure are performed. Significant increases in one or more of the parameters associated with behavior of the animals in the lit area versus behavior in the dark area correspond to active non-sedating anxiolytic compounds.

References:

Young, R.; Johnson, D. N. Soc. Neurosci. Abs. 1988, 14, 207.

Costall, B.; Naylor, R. Brit. J. Pharmacol. 1988, 93, 985–993.

Formula I compounds with the present invention exhibit anxiolytic activity in mice under test conditions. The Example I (R)-isomer produced a 49% increase in the time spent in the lit area at 10 mg/kg IP. The compound of Example II significantly increased the amount of time spent in the lit area (47% to 52%) at doses between 0.1–10 mg/kg IP.

B. Antipsychotic Activity Test

The dopamine hypothesis of schizophrenia attributes some of the symptoms of this illness to a raised mesolimbic dopamine function. In order to mimic the discrete nature of this disturbance in experimental animals, stereotaxic surgery is used to aim dopamine or amphetamine at a discrete mesolimbic nucleus to produce hyperactivity. Test compounds are evaluated for their ability to block this response.

For example, the use of (+)-amphetamine injected intracerebrally into the rat nucleus accumbens increases psychomotor drive which is measured as hyperactivity. Previous studies have shown that this response to amphetamine is selectively blocked by neuroleptic agents or agents having antischizophrenic potential.

Rats are subjected to standard stereotaxic techniques for the implantation of chronically indwelling bilateral guide cannulae for subsequent injections at the center of the nucleus accumbens. Immediately after (+)-amphetamine injection, rats are placed in activity chambers containing infrared photocell units. Hyperactivity is measured as the numbers of interruptions of the photocell beams per unit time.

For dopamine infusion, Alset osmotic mini pumps are implanted into the rats, with subcutaneous polyethylene tubing connecting the pump to the chronically implanted guide cannulae. Over a 13 day period, dopamine is continuously infused into the nucleus accumbens. For an appropriate period of time each day, the locomotor activity is monitored in activity chambers as described above.

Ability of known antischizophrenic agents to antagonize hyperactivity caused by intra-accumbens injection of amphetamine or dopamine is established using fluphenazine and sulpiride. These agents are administered peripherally or intracerebrally prior to administration of amphetamine or daily to those animals with continuous dopamine infusion. Similarly, test compounds are evaluated for their ability to block the hyperactivity produced by amphetamine or dopamine.

Based on profiles of similar compounds in standard pharmacological tests, Formula I compounds of the present invention can exhibit antipsychotic activity in rats under test conditions.

C. Improvement Of Cognitive Function Activity Test

This test allows the measurement of cognitive function in rats. The animals are trained to respond to a single path in a T-maze to obtain a reward (food). The environment then is altered to present a choice of two paths, only one of which leads to the reward. Performance is evaluated by the determination of ratio of correct to incorrect responses and latency to reward for all test paradigms. In addition, performance of rats in the T-maze can be significantly impaired by scopolamine, and compounds are evaluated for their ability to reverse this response.

Male rats, maintained at 85% of normal body weight, are used. The T-maze is constructed of wood and elevated 30 cm from the ground with side arms measuring 60 cm × 10 cm and with start arm measuring 80 cm × 10 cm. A small metal cup, placed towards the end of each side arm, holds the reward pellets. T-maze training consists of paired trials, the first being "forced" in that one side arm is blocked with a wooden barrier while the other is baited. The second is a "choice" trial in which reward pellets are placed in the side arm opposite to that reinforced on the first trial of the pair. A correct choice is recorded when the rat enters the side arm containing the food on the choice trial. The ratio of correct/incorrect choices, and latency to reward are recorded for both forced and choice trials.

The performance of rats in the T-maze can be significantly impaired by the amnestic agent scopolamine. Test compounds are evaluated as antagonists of the disruptive action of scopolamine. Active compounds are those which block the cognitive deficit produced by scopolamine.

Based on profiles of similar compounds in standard pharmacological tests, Formula I compounds of the present invention can exhibit cognition function improvement activity in rats under test conditions.

D. Antagonism Of The von Bezold-Jarisch Reflex

Test compounds were evaluated for antagonism of serotonin induced bradycardia in rats (vonBezold-Jarisch reflex) based on the procedure of Richardson et al. Nature (1985), 316, 126–131. Male Sprague-Dawley rats are anesthesized with urethane and a pressure transducer connected to the carotid artery via a cannula for monitoring the heart rate and blood pressure. Serotonin (10 μg/kg) is given intravenously into the jugular vein, causing bradycardia. After 5 minutes, the test compound is administered intravenously and the reduction of bradycardia determined. Only those rats in which the heart rate is reduced by 50% after administration of serotonin are used. Significant differences are determined according to standard statistical methods.

Formula I compounds of the present invention exhibit 5-HT antagonist activity, and are useful for alleviation of migraine, cluster headache and trigeminal neuralgia symptoms in warm blooded animals.

The compound of Example I reduced the 5-HT induced bradycardia by 86% at 0.0316 mg/kg IV. The Example I (R)-isomer reduced the 5-HT induced bradycardia by 82% at 0.1 mg/kg IV and the Example I (S)-isomer reduced the 5-HT induced bradycardia by 88% at 0.1 mg/kg IV. The compound of Example III reduced the 5-HT induced bradycardia by 70% at 0.0316 mg/kg IV.

E. Effect Of Invention Compounds On Cisplatin-induced Emesis In Dogs

The procedure used to test compounds of the present invention for antiemetic properties is a modification of the method of Gylys et al, Res. Commun, Chem. Pathol. Pharm., 23, 61(1979).

Adult, mongrel, unfasted dogs of both sexes are randomly assigned into treatment groups, with each treatment group consisting of four dogs. On the dosing day all dogs are given cisplatin, 3.0 mg/kg, intravenously. Sixty minutes later, the dogs in the control treatment group are given deionized water, 0.1 ml/kg intravenously. The dogs in the test group are given a test compound at an appropriate dose intraveneously. All doses are administered as a solution by means of a syringe and needle, and each dog's emetic episodes are recorded for 5 hours after the administration of cisplatin.

TABLE E

| Antiemetic (dog) at 1.0 mg/kg IV: % inhibition of cisplatin*-induced emesis | |
|---|---|
| Example Compound | % Inhibition |
| I | 95 |
| I (S)-isomer | 73 (at 0.1 mg/kg) |
| II | 75 |
| III | 93 |
| IV | 94 |

*cis-diammino-dichloro-platinum.

F. Effect Of Invention Compounds On Gastric Emptying Of a Test Meal In Rats

The procedure used to test compounds of the present invention for gastric motility enhancing activity is that of Droppleman et al, J. Pharmacol. Methods, 4, 227(1980).

Each animal is dosed intraperitoneally (9.0 mg/kg) with a test compound or control. After 30 minutes, each animal is given 3 ml of a methylcellulose-based test meal formulation. Sixty minutes after administration of the test meal, each animal is killed by cervical dislocation, and the stomach is removed and weighed. The stomach is cut open, rinsed and dried, and reweighed. The difference between the full and empty weights (amount of meal remaining in stomach) is subtracted from the original test meal weight to determine the meal amount emptied from the stomach during the test period.

TABLE F

| Gastric emptying (rat) at 9.0 mg/kg IP: % change in meal emptied | |
|---|---|
| Example Compound | % Change |
| I | 36 |
| I (R)-isomer | 34% |
| I (S)-isomer | 43% |
| II | 40 |
| III | 21 |
| IV | 24 |
| V | 61 (at 1.0 mg/kg IP) |
| VI | 52 (at 1.0 mg/kg IP) |
| VII | 28 (at 0.10 mg/kg IP) |
| X | 63 (at 10 mg/kg IP) |

What is claimed is:

1. 3-Quinuclidinyl benzamide and benzoate derivatives corresponding to the formula:

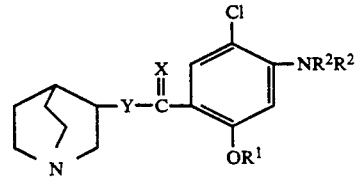

where X is oxygen or sulfur; Y is —NH or —O—; when Y is —O—, $R^1$ is

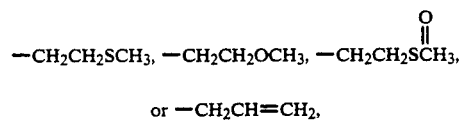

and when Y is —NH, $R^1$ is

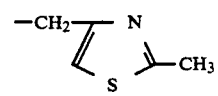

and $R^2$ is hydrogen, $C_1$–$C_4$ alkyl or $C_1$–$C_4$ alkenyl; the geometrical and optical isomers, or a pharmaceutically acceptable salt thereof.

2. A compound according to claim 1 which is selected from:

1-azabicyclo[2.2.2]oct-3-yl 4-amino-5-chloro-2-[2-(methylthio)ethoxy]-benzoate;

1-azabicyclo[2.2.2]oct-3-yl 4-amino-5-chloro-2-(2-methoxyethoxy)benzoate;

1-azabicyclo[2.2.2]oct-3-yl 5-chloro-4-(2-propenylamine)-2-(2-propenyloxy)benzoate;

4-amino-N-(1-azabicyclo[2.2.2]oct-3-yl)-5-chloro-2-[(2-methylthiazol-4-yl)methoxy]benzamide.

3. A method for the treatment of warm blooded animals for anxiety or psychosis symptoms which comprises internally administering to said animals a symptoms alleviating effective amount of a quinuclidine derivative corresponding to the formula:

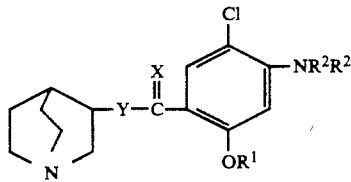

where X is oxygen or sulfur; Y is —NH or —O—; when Y is —O—, R¹ is

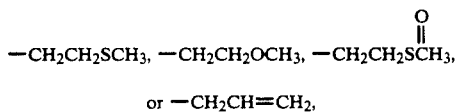

or —CH₂CH=CH₂, and when Y is —NH, R¹ is

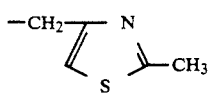

and R² is hydrogen, C₁–C₄ alkyl or C₁–C₄ alkenyl; the geometrical and optical isomers, or a pharmaceutically acceptable salt thereof.

4. A method according to claim 3 where the compound used is selected from the group consisting of:
1-azabicyclo[2.2.2]oct-3-yl 4-amino-5-chloro-2-[2-(methylthio)ethoxy]-benzoate;
1-azabicyclo[2.2.2]oct-3-yl 4-amino-5-chloro-2-(2-methoxyethoxy)benzoate;
1-azabicyclo[2.2.2]oct-3-yl 5-chloro-4-(2-propenylamine)-2-(2-propenyloxy)benzoate; and
4-amino-N-(1-azabicyclo[2.2.2]oct-3-yl)-5-chloro-2-[(2-methylthiazol-4-yl)methoxy]benzamide.

5. A method for the treatment of warm blooded animals for the improvement of cognition function which comprises internally administering to said animals a cognition function improving effective amount of a quinuclidine derivative corresponding to the formula:

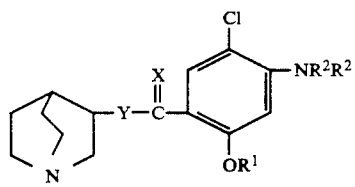

where X is oxygen or sulfur; Y is —NH or —O—; when Y is —O—, R¹ is

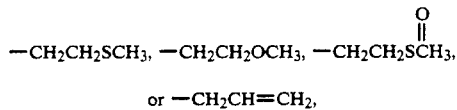

or —CH₂CH=CH₂, and when Y is —NH, R¹ is

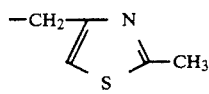

and R² is hydrogen, C₁–C₄ alkyl or C₁–C₄ alkenyl; the geometrical and optical isomers, or a pharmaceutically acceptable salt thereof.

6. A method according to claim 5 where the compound used is selected from the group consisting of:
1-azabicyclo[2.2.2]oct-3-yl 4-amino-5-chloro-2-[2-(methylthio)ethoxy]benzoate;
1-azabicyclo[2.2.2]oct-3-yl 4-amino-5-chloro-2-(2-methoxyethoxy)benzoate;
1-azabicyclo[2.2.2]oct-3-yl 5-chloro-4-(2-propenylamine)-2-(2-propenyloxy)benzoate; and
4-amino-N-(1-azabicyclo[2.2.2]oct-3-yl)-5-chloro-2-[(2-methylthiazol-4-yl)methoxy]benzamide.

7. A method for the treatment of warm blooded animals for migraine, cluster headache or trigeminal neuralgia symptoms which comprises internally administering to said animals a symptoms alleviating effective amount of a quinuclidine derivative corresponding to the formula:

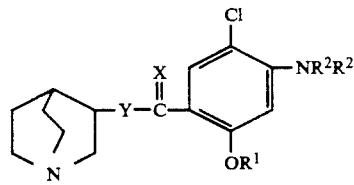

where X is oxygen or sulfur; Y is —NH or —O—; when Y is —O—, R¹ is

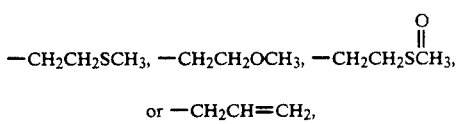

or —CH₂CH=CH₂, and when Y is —NH, R¹ is

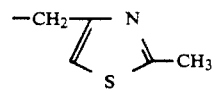

and R² is hydrogen, C₁–C₄ alkyl or C₁–C₄ alkenyl; the geometrical and optical isomers, or a pharmaceutically acceptable salt thereof.

8. A method according to claim 7 where the compound used is selected from the group consisting of:
1-azabicyclo[2.2.2]oct-3-yl 4-amino-5-chloro-2-[2-(methylthio)ethoxy]benzoate;
1-azabicyclo[2.2.2]oct-3-yl 4-amino-5-chloro-2-(2-methoxyethoxy)benzoate;
1-azabicyclo[2.2.2]oct-3-yl 5-chloro-4-(2-propenylamine)-2-(2-propenyloxy)benzoate; and
4-amino-N-(1-azabicyclo[2.2.2]oct-3-yl)-5-chloro-2-[(2-methylthiazol-4-yl)methoxy]benzamide.

9. A method for the treatment of warm blooded animals for emesis caused by administration of anticancer drugs during cancer treatment which comprises internally administering to said animals an emesis-inhibiting effective amount of a quinuclidine derivative corresponding to the formula:

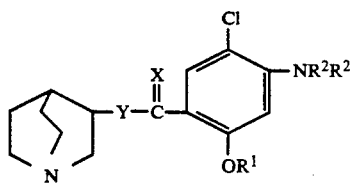

where X is oxygen or sulfur; Y is —NH or —O—; when Y is —O—, R¹ is

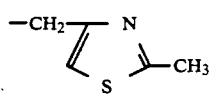

—CH₂CH₂SCH₃, —CH₂CH₂OCH₃, —CH₂CH₂SCH₃, or —CH₂CH=CH₂, and when Y is —NH, Rhu 1 is

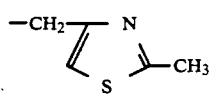

and $R^2$ is hydrogen, $C_1$-$C_4$ alkyl or $C_1$-$C_4$ alkenyl; the geometrical and optical isomers, or a pharmaceutically acceptable salt thereof.

10. A method according to claim 9 where the compound used is selected from the group consisting of:

1-azabicyclo[2.2.2]oct-3-yl 4-amino-5-chloro-2-[2-(methylthio)ethoxy]-benzoate;

1-azabicyclo[2.2.2]oct-3-yl 4-amino-5-chloro-2-(2-methoxyethoxy)benzoate;

1-azabicyclo[2.2.2]oct-3-yl 5-chloro-4-(2-propenylamine)-2-(2-propenyloxy)benzoate; and 4-amino-N-(1-azabicyclo[2.2.2]oct-3-yl)-5-chloro-2-[(2-methylthiazol-4-yl)methoxy]benzamide.

11. A method in accordance with claim 9 wherein the anticancer drug causing emesis is cis-diamminedichloro-platinum.

12. A method in accordance with claim 9 wherein the anticancer drug causing emesis is mechlorethamine hydrochloride.

13. A method in accordance with claim 9 wherein the anticancer drug causing emesis is doxorubicin.

14. A method in accordance with claim 9 wherein the anticancer drug causing emesis is dactinomycin.

15. A method in accordance with claim 9 wherein the anticancer drug causing emesis is dacarbazine.

16. A method for the treatment of warm blooded animals for impared gastrointestinal motility which comprises administering to said animals a gastric motility-enhancing effective amount of a quinuclidine derivative corresponding to the formula:

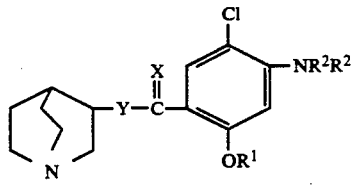

where X is oxygen or sulfur; Y is —NH or —O—; when Y is —O—, R¹ is

—CH₂CH₂SCH₃, —CH₂CH₂OCH₃, —CH₂CH₂SCH₃, or —CH₂CH=CH₂, and when Y is —NH, R¹ is

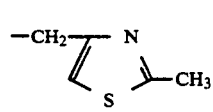

and $R^2$ is hydrogen, $C_1$-$C_4$ alkyl or $C_1$-$C_4$ alkenyl; the geometrical and optical isomers, or a pharmaceutically acceptable salt thereof.

17. A method according to claim 16 where the compound used is selected from the group consisting of:

1-azabicyclo[2.2.2]oct-3-yl 4-amino-5-chloro-2-[2-(methylthio)ethoxy]benzoate;

1-azabicyclo[2.2.2]oct-3-yl 4-amino-5-chloro-2-(2-methoxyethoxy)benzoate;

1-azabicyclo[2.2.2]oct-3-yl 5-chloro-4-(2-propenylamine)-2-(2-propenyloxy)benzoate; and 4-amino-N-(1-azabicyclo[2.2.2]oct-3-yl)-5-chloro-2[(2-methylthiazol-4-yl)methoxy]benzamide.

18. A pharmaceutical composition for the treatment of anxiety, psychosis, cognitive dysfunction, migraine, cluster headache, trigeminal neuralgia, emesis and impaired gastric motility which comprises:

a. a therapeutically effective amount of a compound according to the formula:

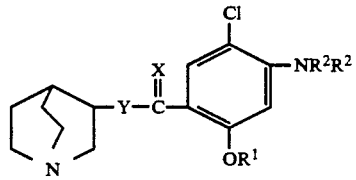

where X is oxygen or sulfur; Y is —NH or —O—; when Y is —O—, R¹ is

—CH₂CH₂SCH₃, —CH₂CH₂OCH₃, —CH₂CH₂SCH₃, or —CH₂CH=CH₂, and when Y is —NH, R¹ is

and $R^2$ is hydrogen, $C_1$-$C_4$ alkyl or $C_1$-$C_4$ alkenyl; the geometrical and optical isomers, or a pharmaceutically acceptable salt thereof, and b. a pharmaceutical carrier thereof.

* * * * *